United States Patent [19]
Makriyannis et al.

[11] Patent Number: 5,489,580
[45] Date of Patent: Feb. 6, 1996

[54] PHOSPHOLIPID COMPOUNDS AND USE THEREFOR

[75] Inventors: Alexandros Makriyannis, Ashford, Conn.; Richard I. Duclos, Jr., Dorchester, Mass.; Donna J. Fournier, Glastonbury, Conn.

[73] Assignee: University of Connecticut, Storrs, Conn.

[21] Appl. No.: 972,138

[22] Filed: Nov. 5, 1992

[51] Int. Cl.$^6$ .......................... A61K 31/21; A61K 31/665; A61K 31/40; C07D 319/12
[52] U.S. Cl. .............................. 514/101; 514/90; 514/91; 544/148; 548/517; 549/221
[58] Field of Search ........................... 549/221; 514/452, 514/101, 90, 91; 548/517; 544/148

[56] References Cited

U.S. PATENT DOCUMENTS 4,444,766  4/1984  Bosies et al. ........................... 424/211

FOREIGN PATENT DOCUMENTS 290197   5/1991  German Dem. Rep. .
3204735  8/1983  Germany .
3239858  1/1984  Germany .

OTHER PUBLICATIONS

S. Tsushima et al., "Syntheses and Antimicrobial Activities of Alkyl Lysophospholipids", *Chem. Pharm. Bull.* 30(9):3260–3270 (1982).

A. Noseda et al., "Effects of Antineoplastic Ether Lipids on Model and Biological Membranes", *Biochimica et Biophysica Acta.* 945:92–100 (1988).

S. Morris–Natschke et al., "Synthesis of Sulfur Analogues of Alkyl Lysophospholipid and Neoplastic Cell Growth Inhibitory Properties", *J. Med. Chem.* 29:2114–2117 (1986).

E. J. Modest et al., "Pharmacological Effects and Anticancer Activity of New Ether Phospholipid Analogs", *In The Pharmacological Effects of Lipids*, pp. 330–337 (1989).

J. Gelas and S. Veyssières–Rambaud, "Hydrogénolyse De 3,6,8–Trioxabicyclo [3.2.1] Octanes Par Le Complexe Aluminohydrure De Lithium–Chlorure D'Aluminium", *Carbohydrate Research*, 37:293–301 (1974).

H. Hayashi et al., "Activation of Guinea Pig Peritoneal Macrophages by Platelet Activating Factor (PAF) and Its Agonists", *J. Biochem.*, 97:1737–1745 (1985).

W. Berdel et al., "Lack of Correlation Between Cytotoxicity of Agonists and Antagonics of Platelet Activating Factor (Paf–acether) in Neoplastic Cells and Modulation of $^3$H–Par–acether Binding to Platelets from Humans in vitro", *Anticancer Research* 7:1181–1187 (1987).

K. Meyer et al., "In Vitro Evaluation of Phosphocholine and Quaternary Ammonium Containing Lipids as Novel Anti–HIV Agents", *J. Med. Chem.* 34:1377–1383 (1991).

Duclos, et al.; J. Org. Chem., 57(23), pp. 6156–6163, (1992); "Synthesis of All Four Stereoisomers which are Conformationally Constrained 1,4–Dioxanyl Analogs of the Antineoplastic Ether Lipid ET–18–OCH$_3$".

*Primary Examiner*—Joseph Paul Brust
*Attorney, Agent, or Firm*—Hamilton, Brook, Smith & Reynolds

[57] ABSTRACT

Novel compounds and use therefor in treating neoplastic and immune system disorders are disclosed. The compound of the present invention comprises a substituted lysophospholipid, which includes a C12 to C20 alkyl ether, a C12 to C20 thioether, or a substituted C3 to C6 heterocycle containing at least two ring heteroatoms, selected from the group consisting of nitrogen, oxygen, sulfur and combinations thereof; and also includes a choline group or a C4 to C7 heterocycle containing heteroatoms selected from the group consisting of nitrogen, oxygen, sulfur and combinations thereof.

The method for treating neoplastic or immune system disorders includes administering an effective dose of a compound of the present invention in a therapeutic manner. Effective doses of these compounds result in cytotoxic effects upon various leukemic cell lines.

The compounds of this invention have the advantage that these compounds possess antineoplastic and immunomodulatory characteristics. Thus, these compound are suited for use, for example, as a drug for the therapeutic treatment of cancers, leukemias and immune system diseases.

12 Claims, No Drawings

PHOSPHOLIPID COMPOUNDS AND USE THEREFOR

BACKGROUND OF THE INVENTION

Many diseases, including those induced by bacterial, viral or environmental exposures, result in prolific neoplastic growth, such as with cancer or leukemia, or in severe immune system degradation, as occurs with acquired immunodeficiency syndrome. Generally, methods for treating these diseases have included surgery, radiation therapy and drug therapy. Among the more effective antineoplastic agents developed are ether lipids, such as 1-O-Octadecyl-2-O-methyl-sn-glycero-3-phosphocholine, and thioether lipids, such as 1-O-Hexadecyl-2-O-methylthioglycero-3-phosphocholine. See, for example, Morris-Natschke et al., *J. Med. Chem.*, 29:2114 (1986); Bosies et al., U.S. Pat. No. 4,444,766, issued Apr. 24, 1984. However, therapeutic treatment with these ether lipid and thioether lipid agents has been noted to result in adverse side effects, for example necrosis of the tail vein and impairment of antibody production in treated mice. See, for example, Kudo et al., *Lipids*, 2.2:862 (1987) and Andreesen, *Prog. biochem. Pharmacol.*, 22:118 (1988).

Therefore, a need exists for new compounds that are therapeutic in the treatment of neoplastic and immune system diseases and that will not cause significant adverse side effects.

SUMMARY OF THE INVENTION

This invention pertains to novel compounds and use therefor in treating neoplastic and immune system disorders. The compounds of the present invention comprises a substituted lysophospholipid, which includes a C12 to C20 alkyl ether, a C12 to C20 thioether, or a substituted C3 to C6 heterocycle containing at least two ring heteroatoms, selected from the group consisting of nitrogen, oxygen, sulfur and combinations thereof; and also includes a choline group or a C4 to C7 heterocycle containing heteroatoms selected from the group consisting of nitrogen, oxygen, sulfur and combinations thereof.

The method for treating neoplastic or immune system disorders includes administering an effective dose of a compound of the present invention in a therapeutic manner. Effective doses of these compounds result in cytotoxic effects upon various leukemic cell lines.

This invention also pertains to a method for forming a heterocyclic lysophospholipid compound of the present invention from a stereoisomer, or racemic mixture, of a 4-alkyl-3,6,8-trioxabicyclo[3.2.1]octane.

The compounds of this invention have the advantage that these compounds possess antineoplastic and immunomodulatory characteristics. Thus, these compounds are suited for use, for example, as a drug for the therapeutic treatment of cancers, leukemias and immune system diseases.

DETAILED DESCRIPTION OF THE INVENTION

The features and other details of the invention, either as steps of the invention or as combinations of parts of the invention, will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention relates to new phospholipid compounds and physiologically acceptable salts thereof, as well as pharmaceutical compositions containing them. Preferred embodiments of the compounds of this invention are represented by the formulae I, II and III shown below:

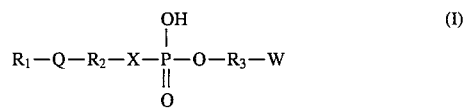

(I)

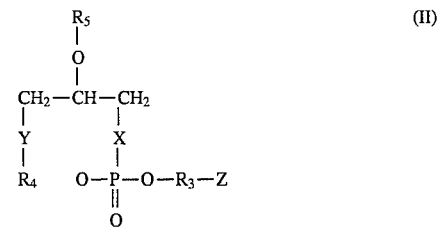

(II)

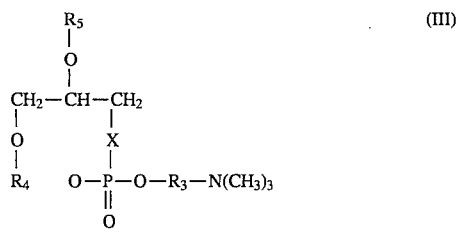

(III)

wherein for each formula shown above, $R_1$ is a C1 to C20 saturated or unsaturated, straight or branched, aliphatic hydrocarbon chain, which can be substituted with one or more substituents selected from the group consisting of a hydroxyl, halogen, alkyl, cycloalkyl, aryl, alkoxy, alkoxycarbonyl, alkylthio and amino.

Q is a C3 to C6 heterocycle containing at least two heteroatoms selected from the group consisting of nitrogen, oxygen, sulfur and combinations thereof, and wherein said saturated heterocycle can be substituted with one or more substituents selected from the group consisting of a hydroxyl, halogen, alkyl, cycloalkyl, aryl, alkoxy, alkoxycarbonyl, alkylthio and amino. In a particularly preferred embodiment, Q is a 1,4-dioxane group, wherein Q is substituted at the 5 position by $R_1$, which is a heptadecyl group, and wherein Q is substituted at the 2 position by $R_3$, which is a methene group.

$R_2$ is a C1 to C2 saturated or unsaturated, alkyl or alkenyl, which can be substituted with one or more substituents selected from the group consisting of a hydroxyl, halogen, alkyl, cycloalkyl, aryl, alkoxy, alkoxycarbonyl, alkylthio and amino.

X is a valency bond, a methylene group (—$CH_2$—) or an oxygen atom. Oxygen is preferred for X.

$R_3$ is a C2 saturated or unsaturated, alkyl or alkenyl, which can be substituted with one or more substituents selected from the group consisting of a hydroxyl, halogen, alkyl, cycloalkyl, aryl, alkoxy, alkoxycarbonyl, alkylthio and amino.

W is an ammonium group, wherein said ammonium group which can be substituted one or more times with a C1 to C6 alkyl radical, or is a C3 to C7 heterocycle containing a nitrogen heteroatom which is bonded to the $R_3$ group, wherein said heterocycle can contain heteroatoms selected from the group consisting of nitrogen, oxygen, sulfur and combinations thereof, and wherein said heterocycle can be substituted with one or more substituents selected from the group consisting of a hydroxyl, halogen, alkyl, cycloalkyl, aryl, alkoxy, alkoxycarbonyl, alkylthio and amino.

$R_4$ is a C12 to C20 saturated or unsaturated, straight or branched, aliphatic hydrocarbon chain, which can be substituted with one or more substituents selected from the group consisting of a hydroxyl, halogen, alkyl, cycloalkyl, aryl, alkoxy, alkoxycarbonyl, alkylthio and amino.

Y is an oxygen or a sulfur atom. In a preferred embodiment, when Y represents an oxygen atom, $R_4$ is a saturated, straight-chain octadecyl group. In another preferred embodiment Y is a sulfur atom and $R_4$ is a saturated, straight-chain hexadecyl group.

$R_5$ is a C1 to C5 saturated or unsaturated, straight or branched, aliphatic hydrocarbon chain. In a preferred embodiment, $R_5$ is a methoxy group.

Z is a C4 to C7 non-aromatic heterocycle containing a nitrogen heteroatom which is bonded to a $R_3$ group, wherein said non-aromatic heterocycle can contain heteroatoms selected from the group consisting of nitrogen, oxygen, sulfur and combinations thereof, and wherein said non-aromatic heterocycle can be substituted with one or more substituents selected from the group consisting of a hydroxyl, halogen, alkyl, cycloalkyl, aryl, alkoxy, alkoxycarbonyl, alkylthio and amino. It is preferred that Y is an oxygen atom and that Z is an N-methylmorpholino or an N-methylpyrrolidino heterocyclic group.

In preferred embodiments, the alkyl, alkoxy, alkoxycarbonyl and alkylthio substituents contain from one to six carbon atoms. A cycloalkyl substituent preferably contains three to six carbon atoms. It is preferred for $R_1$, Q, $R_2$, $R_3$, W, $R_4$ and Z, that a carbon atom or nitrogen atom, included in a chain or ring structure, may contain up to three substituents.

Halogen includes fluorine, chlorine, bromine and iodine.

The physiologically acceptable salts of the compounds of the present invention are obtained by known means, for example, through neutralization of the compounds of the present invention with non-toxic inorganic or organic acids, such as hydrochloric acid, sulfuric acid, phosphoric acid, acetic acid, lactic acid, citric acid, malic acid, salicylic acid, malonic acid, maleic acid or succinic acid.

The invention also pertains to methods for treating neoplastic or immune system disorders. The method comprises administering an effective dose of a compound of the present invention in a therapeutic manner. In one embodiment, an effective dose includes a sufficient amount of one stereoisomer or of a racemic mixture of the compound, where all stereoisomers of said compound possess antineoplastic or immunomodulatory properties. In an alternate embodiment, where only one stereoisomer of a compound possesses significant antineoplastic or immunomodulatory properties, an effective dose comprises a sufficient amount of the pure antineoplastic/immunomodulatory stereoisomer.

The amount of compound in an effective dose depends upon various factors, such as mode of administration, species, age and/or individual condition. An effective dose is usually from about 0.05 to 100 mg/kg of body weight.

In one embodiment, a compound of the present invention is co-administered with an other neoplastic drug, for example adriamycin or mitomycin, for additive antineoplastic effect.

The method of treatment is continued until the neoplastic disorder is in sustained remission or until or the immune system deficiency subsides.

The compounds of the present invention can be administered enterally and parenterally in liquid or solid form. For this purpose, conventional forms of administration, such as tablets, capsules, syrups, suspensions and injections, can be used. Compositions suitable for oral administration can, if desired, contain flavoring and/or sweetening agents.

A method of the present invention relates to a process for forming a new phospholipid compound, and the physiologically acceptable salts thereof, of the composition of Formula I, from a $R_1$-substituted bicycloalkane, which contains three heteroatoms. An acceptable $R_1$-substituted bicycloalkane contains four to seven ring carbons and heteroatoms selected from the group consisting of oxygen, nitrogen and sulfur. In a particularly preferred embodiment, the $R_1$-substituted bicycloalkane is 4-heptadecyl-3,6,8-trioxabicyclo [3.2.1] octane.

Appropriate proportions of $R_1$-substituted bicycloalkane, $LiAlH_4$ and $AlCl_3$ are combined to form a suitable reaction mixture. For example, a reaction mixture composed of $R_1$-substituted bicycloalkane, $LiAlH_4$, and $AlCl_3$ with respective molar ratios of about 73:120:110, would be appropriate.

The reaction mixture is then exposed to conditions sufficient to cleave a bond between a carbon atom and a heteroatom in the $R_1$-substituted bicycloalkane and form a $R_1,R_3$-substituted heterocycle. It is preferred that a carbon-oxygen bond is cleaved. In one embodiment, the $R_1,R_3$-substituted heterocycle formed is 5-alkyl-2-hydroxy methyl-1,4-dioxane.

In a particularly preferred embodiment, the bond between the carbon, at the 5 ring position, and the oxygen, at the 8 ring position, of 4-heptadecyl-3,6,8-trioxabicyclo[3.2.1] octane is cleaved to form the $R_1,R_3$-substituted heterocycle of 5-heptadecyl-2-hydroxymethyl-1,4-dioxane.

The $R_1,R_3$-substituted heterocycle is then extracted with diethyl ether and subsequently dried and evaporated. An appropriate amount of the $R_1,R_3$-substituted heterocycle is added to β-bromoethyl dichlorophosphate, which is in a partially heterogeneous diethyl ether/pyridine solution, and is then maintained under conditions sufficient to form a first product contained in this solution. For example, an acceptable combination of $R_1,R_3$-substituted heterocycle and β-bromoethyl dichlorophosphate is provided by a respective molar ratio of about 45:160.

A suitable amount of water is then added to this solution under conditions sufficient to form a second product. In one embodiment, the second product is (5-alkyl-2-hydroxymethyl-1,4-dioxan-2-yl)methyloxy phospho-(β-bromo)ethanol with heptadecyl particularly preferred as the alkyl component. The second product is then extracted from solution, using, for example, approximately 5:95 v/v methanol/chloroform. The extracted second product is subsequently dried and evaporated to form a white solid second product.

Finally, this second product is dissolved in a suitable solvent and then exposed to excess trimethylamine under conditions sufficient to form an alkylated heterocyclic phospholipid compound. In one embodiment, this alkylated heterocyclic phospholipid compound is (5-alkyl-2-hydroxymethyl-1,4-dioxan-2-yl)methyloxyphosphocholine with heptadecyl particularly preferred as the alkyl component.

The invention will be further illustrated by the following non-limiting examples.

EXEMPLIFICATION

Synthetic Procedures

General Methods

All reactions were carried out under a nitrogen atmosphere. Organic phases were dried over sodium sulfate and evaporated under reduced pressure using a rotoevaporator. Unless stated, all chemicals were obtained from Aldrich Chemical Company or from Sigma Chemical Company, and were used as supplied without further purification. The petroleum hydrocarbons used had a boiling point range of 40° to 60 ° C. The p-toluenesolfonic acid was crystallized from benzene prior to use. Diethyl ether, t-butanol, and trimethylamine, pyridine were each distilled prior to use.

(5-Heptadecyl-1,4-dioxan-2-yl) methyloxy phosphocholines.

To a stirred solution of 2.10 g (18.7 mmol) of potassium tert-butoxide was added a solution of 6.45 (14.8 mmol) of (4R)-2-(1'-bromooctadecyl)-4-hydroxy methyl-1,3-dioxane over a 15 minute period. The mixture was heated to 70° C. overnight and then heated to 90° C. for two additional hours to form a racemic mixture of (1R,4rac,5S)-4-heptadecyl-3, 6,8-trioxabicyclo[3.2.1]octane. The (1R,4S,5S) and (1R,4R, 5S) diastereomers were subsequently separated.

To a stirred solution of 2.10 g (18.7 mmol) of potassium tert-butoxide was added a solution of 6.91 (15.9 mmol) of (4S)-2-(1'-bromooctadecyl)-4-hydroxymethyl-1,3-dioxane over a 15 minute period. The mixture was heated to 70° C. overnight and then heated to 90° C. for two additional hours to form a racemic mixture of (1S,4rac,5R)-(4-heptadecyl-3, 6,8-trioxabicyclo[3.2.1]octane. The (1S,4S,5R) and (1S,4R, 5S) diastereomers were subsequently separated.

For each diastereomer of (4-heptadecyl-3,6,8-trioxabicyclo[3.2.1]octane, 260 mg of the diastereomer (0.73 mmol) was mixed with 48 mg of LiAlH$_4$, in 5 mL of diethyl ether, and then refluxed gently. Dropwise, 15 mg (1.1 mmol) of AlCl$_3$, in 5 mL of diethyl ether was added to the refluxing solution over a 5 minute period. The resulting reaction mixture was then refluxed vigorously over a period of about several hours. The reaction mixture was subsequently cooled to 0° C., quenched by the dropwise addition of ethylacetyl ether, and then mixed with 10 mL of water to form the associated diastereomers of 5-heptadecyl-2-hydroxy methyl-1,4-dioxane. This product was then extracted from the reaction mixture with diethyl ether and the product extract was subsequently dried and evaporated.

To a stirred solution of 0.39 g (1.6 mmol) of β-bromoethyl dichlorophosphate, in 5 mL of diethyl ether, was added 0.6 mL of pyridine over a 2 minute period. After 15 minutes, separately for each diastereomer, a solution of 0.16 (0.45 mmol) of 5-heptadecyl-2-hydroxymethyl-1,4-dioxane was added to the β-bromoethyl dichlorophosphate solution, and then heated to 50° C. for 4 hours. The solution was then cooled to 0° C., 2 mL of water was added, and the solution was stirred for a period of approximately 4 to 8 hours until a clear colorless homogeneous solution formed containing the associated diastereomer of (5-heptadecyl-1,4-dioxan-2-yl)methyloxyphospho(β-bromo)ethanol. This solution was subsequently partitioned and this product was isolated from solution by extracting through use of 5:95 v/v methanol/chloroform and subsequently drying and evaporating the white solid product extract.

Finally, an excess of trimethylamine was evaporated into a stream of nitrogen gas and injected into a glass pressure bottle containing 0.16 g (0.29 mmol) each diastereomer of (5-heptadecyl-1,4-dioxan-2-yl)methyloxyphospho(β-bromo)ethanol, in 20 mL of a 40:40:20 v/v/v chloroform/isopropanol/dimethyl formamide mixture. The contents of the bottle were heated at 50° C. for 48 hours, to form the associated diastereomer [(2R,5S), (2R,5R), (2S,5S) or (2S, 5R)] of (5-heptadecyl-1,4-dioxan-2-yl)methyloxyphosphocholine. The product was then separated by chromatography, evaporation and filtration using a Millipore filter.

Analysis of the (2R,5S)-(5-heptadecyl-1,4-dioxan-2-yl)methyloxyphosphocholine product gave the following results: A melting point (m.p.) of 230° C.; elution ratio for the thin layer chromatography (TLC) (60:30:4 v/v/v CHCl$_3$/CH$_3$OH/H$_2$O) product of R$_f$=0.06; for a $^1$H nuclear magnetic resonance (NMR) run in 1:1 v/v CDCl$_3$/CD$_3$OD with a tetramethylsilane (TMS) reference, shifts of 4.20–4.30 (m, 2 H), 3.90–4.20 (m, 2 H), 3.65–3.85 (m, 2 H), 3.45–3.65 (m, 6 H), 3.23 (s, 9 H), 1.40–1.65 (m, 2 H), 1.26 (br s, 30 H), 0.88 (t, 3 H, J=6.6 Hz); a specific rotation of $[\alpha]^{25}=-6.2°$ (c0.18, 1:1 v/v CHCl$_3$/CH$_3$OH); mass spectra results of m/z 522(MH$^+$), 224, 184, 166; high resolution mass spectra (HRMS) results for C$_{27}$H$_{57}$NO$_6$P(MH$^+$) of m/z 522.3920 with m/z 522.3924 expected; and elemental analysis for C$_{27}$H$_{56}$NO$_6$P-H$_2$O found 59.91 C, 10.99 H and 2.42 N with 60.08 C, 10.83 H and 2.60 N expected.

The structure of (2R,5S)-(5-heptadecyl-1,4-dioxan-2-yl)methyloxyphosphocholine is as follows:

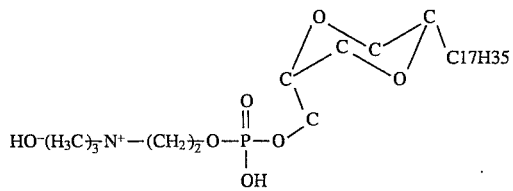

Analysis of the (2R,5R)-(5-heptadecyl-1,4-dioxan-2-yl)methyloxyphosphocholine product gave the following results: A m.p. of 231° C.; elution ratio for the TLC (60:30:4 v/v/v CHCl$_3$/CH$_3$OH/H$_2$O) product of R$_f$=0.06; for a $^1$H NMR run in 1:1 v/v CDCl$_3$/CD$_3$OD with a TMS reference, shifts of 4.20–4.30 (m, 2 H), 3.40–3.95 (m, 10 H), 3.22 (s, 9 H), 1.40–1.65 (m, 2H) 1.26 (br s, 30 H), 0.88 (t, 3 H, J=6.6 Hz); a specific rotation of $[\alpha]^{25}=+3.0°$ (c0.18, 1:1 v/v CHCl$_3$/CH$_3$OH); mass spectra results of m/z 522(MH$^+$), 224, 184, 166; HRMS results for C$_{27}$H$_{57}$NO$_6$P(MH$^+$) of m/z 522.3925 with m/z 522.3924 expected; and elemental analysis for C$_{27}$H$_{57}$NO$_6$P-H$_2$O found 59.79 C, 10.73 H and 2.31 N with 60.08 C, 10.83 H and 2.60 N expected.

The structure of (2R,5R)-(5-heptadecyl-1,4-dioxan-2-yl) methyloxyphosphocholine is as follows:

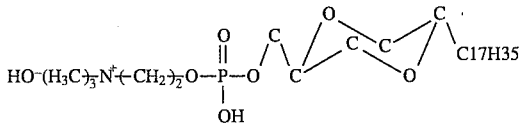

Analysis of the (2S,5R)-(5-heptadecyl-1,4-dioxan-2-yl)methyloxyphosphocholine product gave the following results: A specific rotation of $[\alpha]^{25}=+6.2°$ (c0.18, 1:1 v/v CHCl$_3$/CH$_3$OH) and of $[\alpha]^{25}=+3.0°$ (c0.20, CHCl$_3$); HRMS results for C$_{27}$H$_{57}$NO$_6$P(MH$^+$) of m/z 522.3928 with m/z 522.3924 expected; and elemental analysis for C$_{27}$H$_{56}$NO$_6$P-H$_2$O found 59.76 C, 10.67 H and 2.34 N with 60.08 C, 10.83 H and 2.60 N expected. The structure of (2S,5R)-(5-heptadecyl-1,4-dioxan-2-yl)methyloxyphosphocholine is as follows:

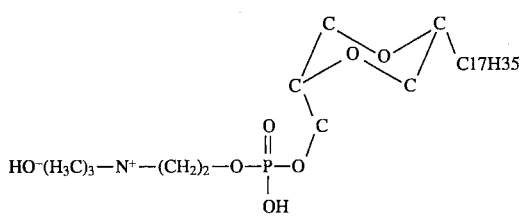

Finally, analysis of the (2S,5S)-(5-heptadecyl-1,4-dioxan-2-yl) methyloxyphosphocholine product gave the following results: A specific rotation of $[\alpha]^{25}=-3.0°$ (c0.18, 1:1 v/v $CHCl_3/CH_3OH$) and of $[\alpha]^{25}=-3.0°$ (c0.20, $CHCl_3$); HRMS results for $C_{27}H_{57}NO_6P(MH^+)$ of m/z 522.3926 with m/z 522.3924 expected; and elemental analysis for $C_{27}H_{56}NO_6P\cdot H_2O$ found 59.89 C, 10.86 H and 2.30 N with 60.08 C, 10.83 H and 2.60 N expected.

The structure of (2S,5S)-(5-heptadecyl-1,4-dioxan-2-yl)methyloxyphosphocholine is as follows:

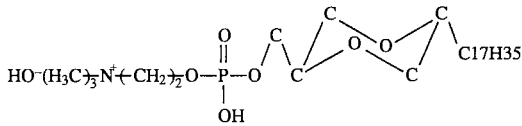

2-O-Methyl-1-O-octadecylglycero-3-phospho-(β-(N-methylpyrrolidino))ethanol.

N-methyl pyrrolidine was quaternized with racemic-2-O-methyl-1-O-octadecylglycero-3-phospho-(β-bromo) ethanol by known procedures for general quaternization to form 2-O-Methyl-1-O-octadecyl glycero-3-phospho-(β-(N-methylpyrrolidino))ethanol. See, for example, Eibl et al., *Chem. Phys. Lipids*, 22:1–8 (1978). The m.p. of this compound was 248° C. The elution ratio for the TLC (60:30:4 v/v/v $CHCl_3/CH_3OH/H_2O$) product was $R_f=0.15$. For a $^1H$ NMR run in $CDCl_3$ with a TMS reference, the shifts observed were 4.15–4.35 (m, 2 H), 3.55–4.10 (m, 8 H), 3.10–3.50 (m, 5 H), 3.29 (s, 3H), 2.10–2.35 (m, 4 H), 1.45–1.65 (m, 2 H), 1.26 (br s, 30 H), 0.88 (t, 3 H, J=6.6 Hz). The mass spectra results were m/z 550(MH$^+$), 250, 210, 192. The HRMS results for $C_{29}H_{61}NO_6P(MH^+)$ was m/z 550.4239 while m/z 550.4237 was expected. Elemental analysis for $C_{29}H_{60}NO_6P\cdot H_2O$ found 61.06 C, 11.25 H, and 2.31 N while 61.35 C, 11.01 H, and 2.47 N were expected.

The structure of 2-O-Methyl-1-O-octadecylglycero-3-phospho-(β-(N-methylpyrrolidino))ethanol is as follows:

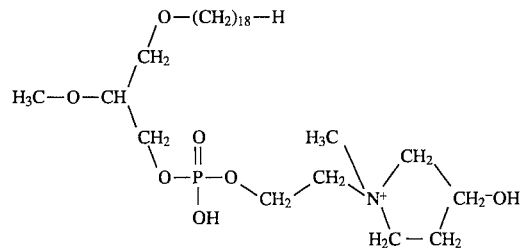

2-O-Methyl-1-O-octadecylglycero-3-phospho-(β-(N-methylmorpholino))ethano].

N-methyl morpholine was quaternized with racemic-2O)-methyl-1-O-octadecylglycero-3-phospho-(β-bromo) ethanol by known procedures for general quarternization to form 2-O-Methyl-1-O-octadecylglycero-3-phospho-(β-(N-methylmorpholino))ethanol. The m.p. observed for this compound was 235°–236° C. The elution ratio for the TLC (60:30:4 v/v/v $CHCl_3/CH_3OH/H_2O$) product was $R_f=0.14$. For a $^1H$ NMR run in $CDCl_3$ with a TMS reference, the shifts observed were 4.25–4.50 (m, 2 H), 3.60–4.25 (m, 12 H), 3.30–3.60 (m, 8 H), 3.44 (s, 3H), 1.45–1.65 (m, 2 H), 1.26 (br s, 30 H), 0.88 (t, 3 H, J=6.6 Hz). The mass spectra results were m/z 566(MH$^+$), 280, 226, 208. The HRMS results for $C_{29}H_{61}NO_7P(MH^+)$ was m/z 566.4180 while m/z 566.4186 was expected. Elemental analysis for $C_{29}H_{60}NO_7P\cdot H_2O$ found 59.90 C, 11.00 H, and 2.35 N while 59.67 C, 10.71 H, and 2.40 N were expected.

The structure of 2-O-Methyl-1-O-octadecylglycero-3-phospho-(β-(N-methylmorpholino))ethanol is as follows:

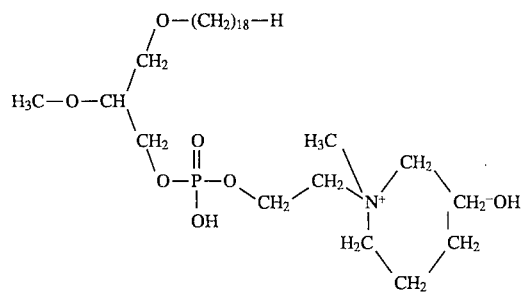

(2R,αR)-2-O-Methyl-1-O-octadecyl-sn-glycero-3-phospho-(α-methyl)choline.

(R)-2-methylcholine tetraphenylborate was prepared from (R)-(–)-1-amino-2-propanol, by known methods. See, for example, Harbison et.al., *J. Lipid Res.*, 25:1140–2 (1984) and Hintze et.al., *Lipids*, 10:20–24 (1975). (R)-2-O-methyl-1-O-octadecyl-sn-glycero-3-phosphoric acid was condensed with (R)-2-methylcholine tetraphenylborate, in the presence of 2,4,6-triisopropylbenzenesulfonyl chloride, to form (2R, αR)-2-O-Methyl-1-O-octadecyl-sn-glycero-3-phospho -(α-methyl)choline, with a m.p. of 83°–86° C. and a decomposition range of 180°–183° C. The elution ratio for the TLC (60:30:4 v/v/v $CHCl_3/CH_3OH/H_2O$) product was $R_f=0.26$. For a $^1H$ NMR run in 2:1 v/v $CDCl_3/CD_3OD$ with a TMS reference, the shifts observed were 4.80–4.85 (m, 1 H), 3.95–4.10 (m, 2 H), 3.30–3.60 (m, 19 H), 1.40–1.60 (m, 5 H), 1.26 (br s, 30 H), 0.88 (t, 3 H, J=6.6 HZ). The specific rotation measured was $[\alpha]^{25}=+2.2°$ (c2.0, $CHCl_3$). The mass spectra results were m/z 538 (MH$^+$) 238, 198, 180. The HRMS results for $C_{28}H_{61}NO_6P(MH^+)$ was m/z 538.4245 while m/z 538.4237 was expected. Elemental analysis for $C_{28}H_{60}NO_6P\cdot 1.25H_2O$ found 59.77 C, 11.26 H and 2.24 N while 60.02 C, 11.07 H and 2.48 N were expected.

The structure of (2R,αR)-2-O-Methyl-1-O-octadecyl-sn-glycero-3-phospho-(α-methyl)choline is as follows:

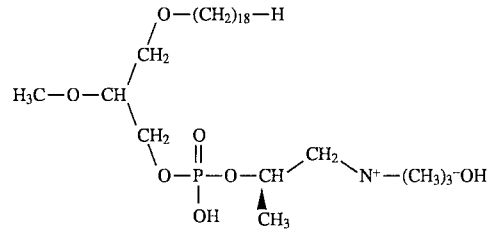

(2R,αS)-2-O-Methyl-1-O-octadecyl-sn-glycero-3-Phospho-(α-methyl)choline.

(S)-2-methylcholine tetraphenylborate was prepared from (S)-(+)-1-amino-2-propanol, by known methods. (R)-2-O-methyl-1-O-octadecyl-sn-glycero-3-phosphoric acid was condensed with (R)-2-methylcholine tetraphenylborate, in the presence of 2,4,6-triisopropylbenzenesulfonyl chloride, to form (2R,αS)-2-O-Methyl-1-O-octadecyl-sn-glycero-3-phospho-(α-methyl)choline, with a m.p. of 91°–94° C. and a decomposition range of 188°–191° C. The elution ratio for the TLC (60:30:4 v/v/v $CHCl_3/CH_3OH/H_2O$) product was $R_f$=0.21. For a $^1H$ NMR run in 2:1 v/v $CDCl_3/CD_3OD$ with a TMS reference, the shifts observed were 4.75–4.85 (m, 1 H), 3.80–4.00 (m, 2 H), 3.30–3.60 (m, 19 H), 1.40–1.60 (m, 5 H), 1.26 (br s, 30 H), 0.88 (t, 3 H, J=6.6 Hz). The specific rotation measured was $[\alpha]^{25}$=− 1.1° (c2.0, $CHCl_3$). The mass spectra results were m/z 538($MH^+$) 238, 198, 180. The HRMS results for $C_{28}H_{61}NO_6P(MH^+)$ was m/z 538.4255 while m/z 538.4237 was expected. Elemental analysis for $C_{28}H_{60}NO_6P \cdot 0.5H_2O$ found 61.46 C, 11.26 H and 2.33 N while 61.51 C, 11.43 H and 2.56 N were expected.

The structure of (2R,αS)-2-O-Methyl-1-O-octadecyl-sn-glycero-3-phospho-(α-methyl)choline is as follows:

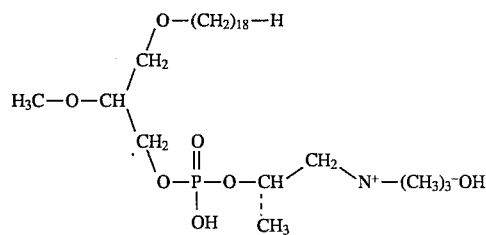

(2R,⊕R) -2-O-Methyl-1-O-octadecyl-sn-glycero-3-phospho -(β-methyl)choline.

(R)-1-methylcholine tetraphenylborate was prepared from (R)-(−)-2-amino-2-propanol, by known methods. (R)-2-O-methyl-1-O-octadecyl-sn-glycero-3-phosphoric acid was condensed with (R)-2-methylcholine tetraphenylborate, in the presence of 2,4,6-triisopropylbenzenesulfonyl chloride, to form (2R,βR)-2-O-Methyl-1-O-octadecyl-sn-glycero-3-phospho-(β-methyl)choline, with a m.p. of 85°–88° C. and a decomposition range of 195°–197° C. The elution ratio for the TLC (60:30:4 v/v/v $CHCl_3/CH_3OH/H_2O$) product was $R_f$=0.25. For a $^1H$ NMR run in 2:1 v/v $CDCl_3/CD_3OD$ with a TMS reference, the shifts observed were 4.25–4.35 (m, 2 H), 3.90–4.05 (m, 2 H), 3.35–3.70 (m, 18 H), 1.40–1.60 (m, 5 H), 1.26 (br s, 30 H), 0.88 (t, 3 H, J=6.6 Hz). The specific rotation measured was $[\alpha]^{25}$=− 6.8° (c2.0, $CHCl_3$). The mass spectra results were m/z 538 ($MH^+$), 238, 198, 180. The HRMS results for $C_{28}H_{61}NO_6P(MH^+)$ was m/z 538.4245 while m/z 538.4237 was expected. Elemental analysis for $C_{28}H_{60}NO_6P \cdot H_2O$ found 60.22 C, 11.14 H and 2.30 N while 60.51 C, 11.24 H and 2.52 N were expected.

The structure of (2R,βR)-2-O-Methyl-1-O-octadecyl-sn-glycero-3-phospho-(α-methyl)choline is as follows:

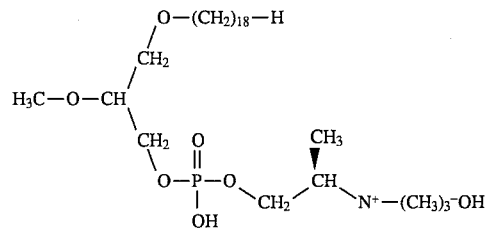

(2R,βS)-2-O-Methyl-1-O-octadecyl-sn-glycero-3-phospho-(β-methyl)choline.

(S)-1-methylcholine tetraphenylborate was prepared from (S)-(+)-2-amino-2-propanol, by known methods. (R)-2-O-methyl-1-O-octadecyl-sn-glycero-3-phosphoric acid was condensed with (R)-2-methylcholine tetraphenylborate, in the presence of 2,4,6-triisopropylbenzenesulfonyl chloride, to form (2R,βS)-2-O-Methyl-1-O-octadecyl-sn-glycero-3-phospho-(β-methyl)choline, with a m.p. of 100°–102° C. and a decomposition range of 200°–203° C. The elution ratio for the TLC (60:30:4 v/v/v $CHCl_3/CH_3OH/H_2O$) product was $R_f$=0.20. For a $^1H$ NMR run in 2:1 v/v $CDCl_3/CD_3OD$ with a TMS reference, the shifts observed were 4.25–4.35 (m, 2 H), 3.85–4.10 (m, 2 H), 3.35–3.70 (m, 18 H), 1.40–1.60 (m, 5 H), 1.26 (br s, 30 H), 0.88 (t, 3 H, J=6.6 Hz). The specific rotation measured was $[\alpha]^{25}$= 5.0° (c2.0, $CHCl_3$). The mass spectra results were m/z 538($MH^+$), 238, 198, 180. The HRMS results for $C_{28}H_{61}NO_6P(MH^+)$ was m/z 538.4255 while m/z 538.4237 was expected. Elemental analysis for $C_{28}H_{60}NO_6P \cdot H_2O$ found 60.25 C, 10.97 H and 2.19 N while 60.51 C, 11.24 H and 2.52 N were expected.

The structure of (2R,βS)-2-O-Methyl-1-O-octadecyl-sn-glycero-3-phospho-(α-methyl)choline is as follows:

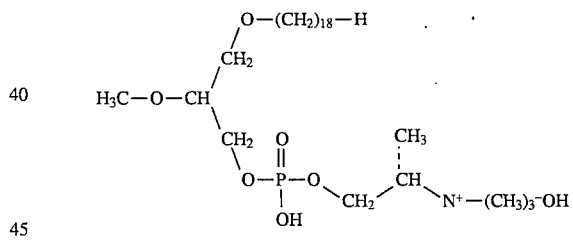

(S)-1-S-hexadecyl-2-O-Methylthioglycero-3-phospho-(βB-(N-methymorpholino))ethanol.

To a stirred solution of 2.76g (11.4 mmol) of β-bromoethyl dichlorophosphate, in 40 mL of diethyl ether, was added 4.5 mL of pyridine over 3 minutes. The mixture was then stirred for an additional 15 minutes. A solution of 1.32 g (3.81 mmol) of (S)-1-S-hexadecyl-2-O-methylthioglycerol, in 60 mL of diethyl ether, as added over a period of one hour and then the mixture was refluxed at 50° C. for 5 hours. The mixture was subsequently cooled to 0° C., mixed with 10 mL of water, and then stirred at ambient temperature. The volume of the mixture was then concentrated to 10 mL and the (S)-1-S-hexadecyl-2-O-methylthioglycero-3-phospho-(β-bromo)ethanol product was extracted with 10:90 v/v methanol/chloroform, dried and subsequently evaporated.

A solution of 400 mg (0.750 mmol) of (S)-1-S-hexadecyl-2-O-methylthioglycero-3-phospho-(β-bromo) ethanol, in 20 mL of 40:40:20 v/v/v chloroform/ iso-propanol/dimethylformamide, was mixed and added to a glass pressure bottle.

An excess of N-methyl morpholine was then added to form a reaction mixture which was subsequently heated at 65° C. for 48 hours to form (S)-1-S-hexadecyl-2-O-Methylthioglycero-3-phospho(β-(N-methymorpholino))ethanol. For a $^1$H NMR run in CDCl$_3$ with a TMS reference, the shifts observed were 4.25–4.45 (m, 2 H), 3.30–4.10 (m, 13 H), 3.46 (s, 3H), 3.41 (s, 3H), 2.60–2.80 (m, 2 H), 2.60–2.80 (m, 2 H), 2.53 (t, 2 H, J=7.3 Hz), 1.45–1.65 (m, 2 H), 1.26 (br s, 26 H), 0.88 (t, 3 H, J=6.6 Hz).

The structure of (S)-1-S-hexadecyl-2-O-methyl-thioglycero-3-phospho-(β-(N-methymorpholino))ethanol is as follows:

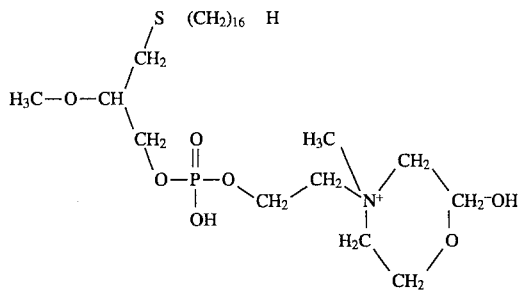

(R)-2-O-Methyl-1-O-octadecylglycero-3-phosphoric acid.

A solution of 6.81 g (25.4 mmol) of chlorodiphenylphosphate, in 35 mL of pyridine, was mixed with a solution of 5.60 g (15.6 mmol) of(S)-2-O-Methyl-1-O-octadecyl-sn-glycerol, in 100 mL of pyridine, and then stirred for 20 hours. Then 10 mL of water were added and the mixture was subsequently stirred for an additional 20 minutes. The mixture was then partitioned between 80 mL of water and 80 mL of diethyl ether. The resulting diethyl ether fraction was sequentially washed with 30 mL of 0.5 N HCl, 25 mL of water, 25 mL of sodium bicarbonate, and additional water until the pH of this fraction was approximately neutral. The washed diethyl ether fraction was then dried and evaporated to yield liquid (R)-2-O-Methyl-1-O-octadecyl-sn-glycero-3-phosphoric acid diphenyl ester.

Subsequently, 8.23 g (13.9 mmol) of (R)-2-O-Methyl-1-O-octadecyl-sn-glycero-3-phosphoric acid diphenyl ester was mixed with 0.79 g (3.5 mmol) of a platinum oxide catalyst, which was in 50 mL of a 25:75 v/v chloroform/ethanol solution, and then mechanically shaken under 25 psi on a Parr apparatus for 10 hours. Following separation of the platinum oxide catalyst by filtration the resultant organic phase was washed with 10 mL of a 90:10 v/v water/methanol mixture. The organic phase was then dried, evaporated, and stored in a desiccator over P$_2$O$_5$ for 3 days at a pressure of 0.1 mm Hg to form 6.01 g (13.7 mmol) of white, solid (R)-2-O-Methyl-1-O-octadecyl-sn-glycero-3-phosphoric acid. Thus a yield of 98% of the desired compound, with a melting point (m.p.) of 59°–60° C., was obtained. The elution ratio for the TLC (80:13:8:0.3 v/v/v/v CHCl$_3$/CH$_3$OH/CH$_3$COOH/H$_2$O) product was R$_f$=0.20. For a $^1$H NMR run in CDCl$_3$ with a TMS reference, the shifts observed were 4.13 (m, 2 H), 3.40–3.70 (m, 8 H), 1.40– 1.60 (m, 2 H), 1.26 (br s, 30 H), 0.88 (t, 3 H, J=6.6 Hz). The specific rotation measured was [α]$^{25}$=+1.0° (c0.49, CHCl$_3$). The mass spectra results were m/z 439 (MH$^+$), 390, 169, 133. The HRMS results for C$_{22}$H$_{48}$O$_6$P (MH$^+$) was m/z 439.3198 while m/z 439.3189 was expected. Elemental analysis for C$_{22}$H$_{47}$O$_6$P found 59.96 C, and 10.62 H while 59.25 C and 10.80 H were expected.

The structure of (R)-2-O-Methyl-1-O-octadecylglycero-3-phosphoric acid is as follows:

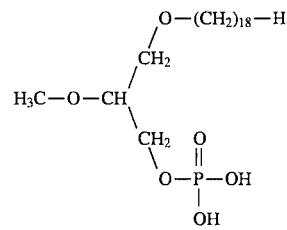

Cytotoxic Analysis

The compounds of the present invention were tested for their cytotoxic effects upon various leukemic cell lines. The effectiveness of each of the compounds tested was measured through assessing the leakage of the cytosolic enzyme, lactic dehydrogenase (LDH), from the leukemia cells into the media following incubation with the compound.

The LDH release assay used was a modified microtiter plate enzyme linked immunosorbent assay LDH release assay. Seven mg of each phospholipid compound to be tested was completely dissolved in separate 700 μL volumes of 100% ethanol. The ethanolic solutions were then diluted to form stock solutions by the addition of 70 mL RPMI complete medium until the concentration of phospholipid in each solution was lowered to about 100 μg/mL. An RPMI complete medium contains a RPMI 1640 medium, without red phenol, 20 mM Hepes buffer, 2 mM L-glutamine, 50 μM 2-mercaptoethanol and 20% of fetal calf serum. To form an ethanol control, a 350 μL aliquot of ethanol was added to a small glass bottle containing 35 mL of RPMI complete medium.

Each stock solution was mixed by magnetic stirring bar at room temperature for one hour and then filtered through a 0.22 μm Millipore filter, where the filter was pre-rinsed with 0.6 mL of RPMI complete medium. The stock solutions were subsequently placed in a shaker in a cold room overnight and subsequently stored in small glass bottles wrapped with aluminum foil at 4° C.

Each stock solution was shaken for 30 minutes at room temperature. Then each phospholipid stock solution was separately diluted, in small glass vials, with RPMI complete medium to form solutions with phospholipid concentrations of 80 μg, 40 μg, 20 μg and 10 μg.

For each cell line, the leukemia cells were removed from the culture flask, put into a 50 mL conical tube, centrifuged at 500 rpm for 10 minutes and then washed once with fresh RPMI 1640 medium. The viable cells were counted using a trypan blue exclusion test and then diluted to form a cell suspension with a concentration of 1×10$^6$ cells/mL by adding an RPMI medium which contained RPMI 1640 medium which contains 20 mM Hepes buffer, 2 mM L-glutamine and 50 μM 2-mercaptoethanol but does not include phenol red or fetal calf serum.

Aliquots (0.4 mL) of each 100 μg, 80 μg, 40 μg, 20 μg and 10 μg phospholipid solution were added to small vials containing 0.4 mL of cell suspension to form test solutions with phospholipid concentrations of 50, 40, 20, 10 and 5 μg/mL; cell densities of 5×10$^5$ cells/mL; and 10% fetal calf serum in RPMI complete medium. For an ethanol control group, an aliquot of 0.4 mL of the ethanol control was mixed with 0.4 mL of cell suspension to form a control group with an ethanol concentration of 0.495% and a cell density of 5×10⁵ cells/mL. For a negative control group, a 0.4 mL aliquot of RPMI complete medium was added to 0.4 mL of cell suspension to give a cell density of 5×10⁵ cells/mL. For a positive control group, cell suspension was diluted with RPMI 1640 medium, which contained 10% fetal calf serum, 20 mM Hepes buffer, 2 mM L-glutamine and 2-mercaptoethanol and stored overnight at −70° C.

Aliquots (0.2 mL) of each test solution and control group were added to flat bottomed Linbro microtiter plates, in triplicate, and incubated for 2, 4, 8 and 24 hours. Following incubation, the plates were centrifuged at 500 rpm for 5 minutes. Supernatant aliquots of 0.1 mL were then transferred to separate wells on an optic-clear, flat-bottomed microtiter plate. A volume of 0.1 mL of an LDH substrate mixture, containing $5.4 \times 10^{-2}$ M L(+)-lactate, $6.6 \times 10^{-4}$ M MINT, provided by Sigma Chemical Company, $2.8 \times 10^{-4}$ M PMS, and $1.3 \times 10^{-3}$ M NAD in a 0.2 M Tris buffer of pH 8.2, was added to each well. A Linbro-Titertek Company Lambda microtiter plate reader was used to monitor the absorbance at 490 nm.

The cytotoxic effectiveness of each compound tested, as provided in Table I, is described in terms of the $ID_{50}$ of the drug. The $ID_{50}$ is the concentration of the compound tested that is required to produce a cytotoxicity that is 50% of the control's cytotoxicity.

TABLE I

| Compound | $ID_{50}^a$ (μg/ml) | $ID_{50}^b$ (μg/ml) | $ID_{50}^c$ (μg/ml) | $ID_{50}^d$ (μg/ml) |
|---|---|---|---|---|
| (2R,5S)-(5-heptadecyl-1,4-dioxan-2-yl) methyloxyphosphocholine | <2.0 | — | <2.0 | <2.0 |
| (2R,5R)-(5-heptadecyl-1,4-dioxan-2-yl) methyloxyphosphocholine | 4.0 | — | 4.0 | 4.0 |
| (2S,5R)-(5-heptadecyl-1,4-dioxan-2-yl) methyloxyphosphocholine | 4.0 | — | 4.0 | 4.0 |
| (2S,5S)-(5-heptadecyl-1,4-dioxan-2-yl) methyloxyphosphocholine | <2.0 | — | <2.0 | <2.0 |
| 2-O-methyl-1-O-octadecylglycero-3-phospho-(β-(N-methyl-pyrrolidino))ethanol | 3.4 | 13.0 | — | 17.5 |
| 2-O-methyl-1-O-octadecylglycero-3-phospho-(β-(N-methyl-morpholino))ethanol | 3.6 | 6.6 | — | 11.0 |
| (2R,αR)-2-O-methyl-1-O-octadecyl-sn-glycero-3-phospho (α-methyl)choline | 5.6 | 21.0 | — | 22.0 |
| (2R,αS)-2-O-methyl-1-O-octadecyl-sn-glycero-3-phospho (α-methyl)choline | 4.5 | 15.2 | — | 21.5 |
| (2R,βR)-2-O-methyl-1-O-octadecyl-sn-glycero-3-phospho (β-methyl)choline | 3.3 | 11.2 | — | 13.5 |
| (2R,βS)-2-O-methyl-1-O-octadecyl-sn-glycero-3-phospho (β-methyl)choline | 2.85 | 6.6 | — | 12.8 |
| (R)-2-O-methyl-1-O-octadecyl-sn-glycero-3-phosphoric acid | 2.95 | 3.0 | — | 24.0 |

ᵃCEM leukemic cell line.
ᵇHUT 78 leukemic cell line.
ᶜHL-60 leukemic cell line.
ᵈNAMALWA leukemic cell line.
Note:
All leukemic cells are available from the American Tissue Culture Collection, Rockville, MD (ATCC).

Equivalents

Those skilled in the art will recognize, or be able to ascertain, using no more than routine experimentation, many equivalents to specific embodiments of the invention described specifically herein. Such equivalents are intended to be encompassed in the scope of the following claims.

We claim:

1. A compound represented by the formula:

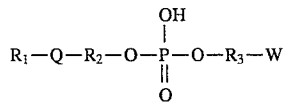

and physiologically acceptable salts thereof, wherein $R_1$ is a straight or branched, aliphatic hydrocarbon chain, which contains up to 20 carbon atoms in said hydrocarbon chain, which may contain one or more carbon-carbon double bonds, and which may be substituted with one or more substituents selected from the group consisting of hydroxyl, C1 to C6 alkyl, C3 to C6 cycloalkyl, C1 to C6 alkoxy, C1 to C6 alkylthio and amino;

Q is a C3 to C4 heterocycle containing at least two ring oxygen atoms as the only ring hetero atoms, wherein said heterocycle may be substituted with one or more C1 to C6 alkyl substituents;

$R_2$ is a methylene radical, which may be substituted with one or more C1 to C6 alkyl substituents;

$R_3$ is a C2 alkyl or alkenyl, which may be substituted with one or more C1 to C6 alkyl substituents;

W is an ammonium group, wherein said ammonium group may be substituted one or more times with a C1 to C6 alkyl radical, or is a C3 to C7 heterocyclic amine having a nitrogen heteroatom which is bonded to the $R_3$ group, wherein said heterocycle may be substituted with one or more substituents selected from the group consisting of a C1 to C6 alkyl, C3 to C6 cycloalkyl, C1 to C6 alkoxy, C1 to C6 alkoxycarbonyl, and C1 to C6 alkylthio.

2. A compound represented by the formula:

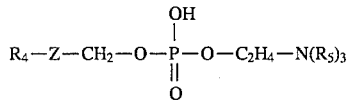

and physiologically acceptable salts thereof, wherein $R_4$ is a straight or branched, aliphatic hydrocarbon chain, which contains up to 20 carbon atoms in said hydrocarbon chain;

Z is a dioxanyl group; and $R_5$ is —H or C1 to C6 alkyl radical, wherein each $R_5$ is independently selected.

3. The compound of claim 2 designated (2R,5S)-(5-heptadecyl-1,4-dioxan-2-yl)methyloxyphosphocholine.

4. The compound of claim 2 designated (2R,5R)-(5-heptadecyl-1,4-dioxan-2-yl)methyloxyphosphocholine.

5. The compound of claim 2 designated (2S,5R)-(5-heptadecyl-1,4-dioxan-2-yl)methyloxyphosphocholine.

6. The compound of claim 2 designated (2S,5S)-(5-heptadecyl-1,4-dioxan-2-yl)methyloxyphosphocholine.

7. A pharmaceutical composition having antitumor or immunomodulatory activity comprising a pharmaceutically acceptable carrier and an effective mount of a compound represented by the formula:

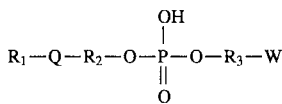
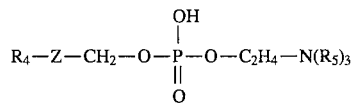

and physiologically acceptable salts thereof, wherein $R_1$ is a, straight or branched, aliphatic hydrocarbon chain, which contains up to 20 carbon atoms in said hydrocarbon chain, which may contain one or more carbon-carbon double bonds, and which may be substituted with one or more substituents selected from the group consisting of hydroxyl, C1 to C6 alkyl, C3 to C6 cycloalkyl, C1 to C6 alkoxy, C1 to C6 alkylthio and amino;

Q is a C3 to C4 heterocycle containing at least two ring oxygen atoms as the only ring hetero atoms, wherein said heterocycle may be substituted with one or more C1 to C6 alkyl substituents;

$R_2$ is a methylene radical, which may be substituted with one or more C1 to C6 alkyl substituents;

$R_3$ is a C2 alkyl or alkenyl, which may be substituted with one or more C1 to C6 alkyl substituents;

W is an ammonium group, wherein said ammonium group may be substituted one or more times with a C1 to C6 alkyl radical, or is a C3 to C7 heterocyclic amine having a nitrogen heteroatom which is bonded to the $R_3$ group, wherein said heterocycle may be substituted with one or more substituents selected from the group consisting of a C1 to C6 alkyl, C3 to C6 cycloalkyl, C1 to C6 alkoxy, C1 to C6 alkoxycarbonyl, and C1 to C6 alkylthio.

8. A pharmaceutical composition having antitumor or immunomodulatory activity comprising a pharmaceutically acceptable carrier and an effective amount of a compound represented by the formula:

and physiologically acceptable salts thereof, wherein $R_4$ is a straight or branched, aliphatic hydrocarbon chain, which contains up to 20 carbon atoms in said hydrocarbon chain;

Z is a dioxanyl group; and $R_5$ is —H or C1 to C6 alkyl radical, wherein each $R_5$ is independently selected.

9. The composition of claim 8, wherein said compound is selected from the group consisting of:

(2R,5S)-(5-heptadecyl-1,4-dioxan-2-yl) methyloxyphosphocholine;

(2R,5R)-(5-heptadecyl-1,4-dioxan-2-yl) methyloxyphosphocholine;

(2S,5R)-(5-heptadecyl-1,4-dioxan-2-yl) methyloxyphosphocholine; and (2S,5S)-(5-heptadecyl-1,4-dioxan-2-yl) methyloxyphosphocholine.

10. A method for treating neoplastic or immune system disorders, comprising administering an effective amount of the compound of claim 1, in a effective manner.

11. A method for treating neoplastic or immune system disorders, comprising administering an effective amount of the compound of claim 2, in a therapeutically effective manner.

12. A method for treating neoplastic or immune system disorders, comprising administering an effective amount of (5-heptadecyl-1,4-dioxan-2-yl)methyloxyphosphocholine in a therapeutically effective manner.

* * * * *

UNITED STATES PATENT AND TRADEMARK OFFICE
CERTIFICATE OF CORRECTION

PATENT NO. : 5,489,580
DATED : February 6, 1996
INVENTOR(S) : Alexandros Makriyannis, et al It is certified that error appears in the above-indentified patent and that said Letters Patent is hereby corrected as shown below:

Column 15:
    Claim 7, Col. 15, line 8, delete the comma after "$R_1$ is a".
Column 16:

Claim 10, line 26, after "a", insert ---therapeutically---.

Signed and Sealed this

Thirteenth Day of August, 1996

Attest:

BRUCE LEHMAN

*Attesting Officer*    *Commissioner of Patents and Trademarks*